United States Patent
Wilk et al.

(10) Patent No.: US 7,122,705 B2
(45) Date of Patent: Oct. 17, 2006

(54) METHOD FOR PREPARING 3-CYCLOPENTYLOXY-4-METHOXYBENZALDEHYDE

(75) Inventors: Bogdan Kazimierz Wilk, New City, NY (US); Nalukui Mwisiya, Chester, NY (US); Jean Louise Helom, Hillsdale, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/100,862

(22) Filed: Apr. 7, 2005

(65) Prior Publication Data

US 2005/0228199 A1    Oct. 13, 2005

Related U.S. Application Data

(60) Provisional application No. 60/560,575, filed on Apr. 8, 2004.

(51) Int. Cl.
*C07C 45/71* (2006.01)
(52) U.S. Cl. .................. 568/426; 568/433; 568/437
(58) Field of Classification Search .................... None
See application file for complete search history.

(56) References Cited

U.S. PATENT DOCUMENTS

| | | | |
|---|---|---|---|
| 4,102,495 | A | 7/1978 | Flynn et al. |
| 4,308,278 | A | 12/1981 | Schneider et al. |
| 5,124,455 | A | 6/1992 | Lombardo |
| 5,250,700 | A | 10/1993 | Bagli et al. |
| 5,459,151 | A | 10/1995 | Lombardo |
| 5,665,737 | A | 9/1997 | Cavalla et al. |
| 5,866,593 | A * | 2/1999 | Warrellow et al. .......... 514/336 |
| 6,518,306 | B1 | 2/2003 | Christensen, IV |

OTHER PUBLICATIONS

Alexander et al. CDP840. A Prototype of a Novel Class of Orally Active Anti-Inflammatory Phoshodiesterase 4 Inhibitors. Bioorganic & Medicinal Chemistry Letters, 2002, vol. 12, p. 1451-1456.*
Itokawa et al., Studies on Antitumor Cyclic Hexapeptides RA Obtained from Rubiae Radix, Rubiaceae. III. On Derivatives of RA-V and Their in vivo Activities, Chem. Pharm. Bull (Tokyo), 32(8): 3216 (Aug. 1984).
Itokawa et al., Studies on Antitumor Cyclic Hexapeptides RA Obtained from Rubiae Radix, Rubiaceae. III. On Derivatives of RA-V and Their in vivo Activities, Chem. Pharm. Bull (Tokyo), 32(8): 3216 (Aug. 1984) (Beilstein Abstract—Accession No. 1615269).
Coastes et al., "Cyclic Nucleotide Phosphodiesterase Inhibition by Imidazopyridines: Analogues of Sulmazole and Isomazole as Inhibitors of the cGMP Specific Phosphodiesterase", J. Med. Chem., 36:1387-1392 (May 14, 1993).
Coastes et al., "Cyclic Nucleotide Phosphodiesterase Inhibition by Imidazopyridines: Analogues of Sulmazole and Isomazole as Inhibitors of the cGMP Specific Phosphodiesterase", J. Med. Chem., 36:1387-1392 (May 14, 1993) (Beilstein Abstract—Accession No. 3864124).

* cited by examiner

*Primary Examiner*—Sikarl A. Witherspoon
(74) *Attorney, Agent, or Firm*—Howson and Howson; Arnold S. Milowsky

(57) ABSTRACT

Processes for coupling phenol and cycloalkyls including combining an optionally substituted phenol, a cycloalkyl substituted with a leaving group, carbonate salt, tetrahydrofuran, and an optional phase transfer agent are provided. Also provided are processes for preparing 3-cyclopentyloxy-4-methoxybenzaldehyde by combining 3-hydroxy-4-methoxybenzaldehyde, a cyclopentyl compound, a carbonate salt, a solvent, and an optional phase transfer agent.

23 Claims, No Drawings

METHOD FOR PREPARING 3-CYCLOPENTYLOXY-4-METHOXYBENZALDEHYDE

CROSS-REFERENCE TO RELATED APPLICATIONS

This application claims the benefit under 35 USC 119(e) of prior U.S. Provisional Patent Application No. 60/560,575, filed Apr. 8, 2004.

BACKGROUND OF THE INVENTION

The present invention is drawn to processes for coupling phenols and optionally substituted cycloalkyls.

3-Cyclopentyloxy-4-methoxybenzaldehyde (formula I) is a key intermediate in the preparation of compounds that are useful in the treatment of asthma, inflammatory disorders including psoriasis, proliferative skin disease, Crohns disease, urticaria, rhinitis, arthritis and neurogenic inflammation, and depression.

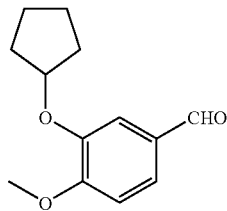

I

One current preparation of 3-cyclopentyloxy-4-methoxybenzaldehyde includes alkylating 3-hydroxy-4-methoxybenzaldehyde (isovanillin) with cyclopentyl bromide in a solvent such as N,N-dimethylformamide (DMF), acetone or acetonitrile (MeCN) in the presence of anhydrous potassium or cesium carbonate. However, product isolation from the reaction mixture is cumbersome, especially on a large scale. Specifically, in order to isolate 3-cyclopentyloxy-4-methoxybenzaldehyde, an aqueous work-up must be performed including the addition of water, extraction, separation, and drying to give variable yields of 3-cyclopentyloxy-4-methoxybenzaldehyde. The compound of formula I can then be utilized in further reactions.

The solvents utilized during alkylation of isovanillin are also incompatible with the reagents used in certain subsequent reactions. For example, DMF, acetone or MeCN can react with organometallic reagents, ylides, glycidyl esters, and carbanions, among reagents. These organometallic reagents, ylides, glycidyl esters, and carbanions usually require anhydrous conditions and anhydrous solvents, such as tetrahydrofuran (THF). It is therefore necessary to isolate 3-cyclopentyloxy-4-methoxybenzaldehyde from the DMF, acetone, or MeCN prior to performing subsequent steps.

What is needed in the art are other methods for preparing compounds of formula I.

SUMMARY OF THE INVENTION

In one aspect, the present invention provides processes for coupling phenol and cycloalkyl compounds.

In another aspect, the present invention provides processes for preparing 3-cyclopentyloxy-4-methoxybenzaldehyde.

Other aspects and advantages of the present invention are described further in the following detailed description of the preferred embodiments thereof.

DETAILED DESCRIPTION OF THE INVENTION

The present invention provides a simple, environmentally-friendly, and a low-cost process for the preparation of 3-cyclopentyloxy-4-methoxybenzaldehyde. Further, the present invention also provides for the preparation of 3-cyclopentyloxy-4-methoxybenzaldehyde in a solvent that can be used in situ, i.e., taken directly to a next step. By doing so, the lengthy and cumbersome workup, isolation and drying of 3-cyclopentyloxy-4-methoxybenzaldehyde can be avoided.

Thus, 3-cyclopentyloxy-4-methoxybenzaldehyde can efficiently be utilized in further reactions, such as Wittig olefination reaction, reaction with organometallic species such as Grignard reagents, alkyllithium, or aryllithium reagents; reaction with carbanions; oxidations; reductions; hydrocyanation; acetalization; bisulfite addition; reductive amination; demethylation; aromatic electrophilic substitution; among further reactions known to those of skill in the art.

I. Definitions

The term "alkyl" is used herein as a group or part of a group to refer to both straight- and branched-chain saturated aliphatic hydrocarbon groups having 1 to about 10 carbon atoms, or about 1 to about 8 carbon atoms. The term "alkenyl" is used herein to refer to both straight- and branched-chain alkyl groups having one or more carbon-carbon double bonds and containing about 2 to about 10 carbon atoms. In one embodiment, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bonds and having 2 to about 8 carbon atoms. In one embodiment, the term alkynyl refers to an alkyl group having 1 or 2 carbon-carbon triple bonds and having 2 to about 6 carbon atoms.

The terms "substituted alkyl" refers to an group having one or more substituents including, without limitation, halogen, CN, OH, $NO_2$, amino, aryl, heterocyclic, alkoxy, aryloxy, alkylcarbonyl, alkylcarboxy, and arylthio which groups can be optionally substituted. These substituents can be attached to any carbon of an alkyl, alkenyl, or alkynyl group provided that the attachment constitutes a stable chemical moiety.

The term "aryl" as used herein as a group or part of a group, e.g., aryloxy, refers to an aromatic system, e.g., of 6 to 14 carbon atoms, which can include a single ring or multiple aromatic rings fused or linked together where at least one part of the fused or linked rings forms the conjugated aromatic system. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom-containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted heterocyclic group is substituted with 1 to about 4 substituents.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "leaving group" as used herein refers to a substituent that is present on a chemical compound and can be displaced. The particular leaving group utilized in the present invention is dependent upon the specific reaction being performed and can readily be determined by one of skill in the art. Common leaving groups include, without limitation, halides, triflates (OTf), boron moieties including boronic acids and trihaloborate salts such as trifluoroborate salts ($BF_3^-$), zinc halides, magnesium moieties, diazonium salts ($N_2^+$), tosylates (OTs) and other sulfonic esters, mesylates (OMs), and copper moieties. In one embodiment, the leaving group is a halide such as bromine, chlorine, or iodine; OTosylate; OMesylate; and OTriflate. In another embodiment, the leaving group is bromine.

The term "phase transfer agent" as used herein refers to a chemical compound that increases the rate of the coupling reaction. Numerous phase transfer agents are known in the art and are readily available. Examples of phase transfer agents include, without limitation, ammonium salts. In one embodiment, the phase transfer agent includes tetraalkylammonium salts. In another embodiment, the phase transfer agent includes tetrabutylammonium salts. In yet another embodiment, the phase transfer agent includes tetrabutylammonium halide salts. In still another embodiment, the phase transfer agent includes tetrabutylammonium bromide ($Bu_4NBr$).

The term "purified" or "pure" as used herein refers to a compound that contains less than about 10% impurities. In one embodiment, the term "purified" or "pure" refers to a compound that contains less than about 5% impurities, less than about 2.5% impurities, less than about 2% impurities, less than about 1.5% impurities, and less than about 1% impurities. In another embodiment, the impurities are in the range of 1.6 to 2.4%. The term "purified" or "pure" can also refer to a compound that contains about 0% impurities.

II. Methods of the Present Invention

The present invention therefore provides processes for coupling an optionally substituted phenol and cycloalkyl. See, Scheme 1.

Scheme 1

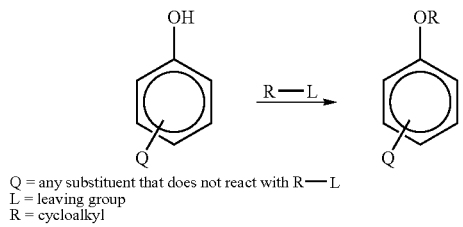

Q = any substituent that does not react with R—L
L = leaving group
R = cycloalkyl The optionally substituted phenol can first be combined with a cycloalkyl substituted with a leaving group, a carbonate salt, and a solvent.

The phenol utilized according to the present invention can be an unsubstituted or phenol substituted with one or more substituents as defined above for substituted aryl that do not react with the reagents utilized during the coupling reaction. One of skill in the art would readily be able to select the particular phenol for use in the present invention. In one embodiment, the phenol is optionally substituted with a methoxy group, among other substituents. In another embodiment, the phenol is optionally substituted with methoxy and C(O)H groups. In a further embodiment, the phenol is 3-hydroxy-4-methoxybenzaldehyde, or a derivative thereof.

The cycloalkyl used in the present invention is a saturated hydrocarbon group that is cyclic in structure and has about 3 to about 10 carbon atoms, about 5 to about 8 carbon atoms, or about 5 carbon atoms. The cycloalkyl has a leaving group, as described above, attached to a carbon-atom of the cyclic structure. The cycloalkyl group can also be optionally substituted with any substituent that does not interfere with the coupling reaction and can be readily selected by one of skill in the art and can include alkyl, halogen, CN, OH, $NO_2$, amino, aryl, heterocyclic, alkoxy, aryloxy, alkylcarbonyl, alkylcarboxy, and arylthio substituents, which groups can be optionally substituted. The substituents can be attached to any carbon atom of the cycloalkyl ring provided that the attachment constitutes a stable chemical moiety.

In one embodiment, the cycloalkyl is an optionally substituted cyclopropyl, cyclobutyl, cyclopentyl, or cyclohexyl group, and in another embodiment is an optionally substituted cyclopentyl group of the formula CpX, wherein X denotes a leaving group as previously described. In yet another embodiment, the cycloalkyl is cyclopentyl bromide. See, Scheme 2.

Scheme 2

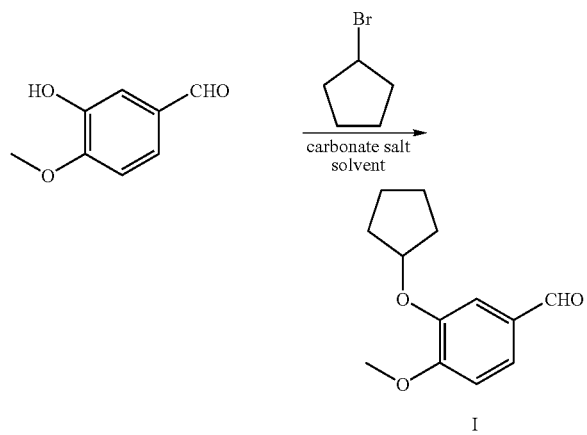

In one embodiment, an excess of the cycloalkyl is utilized in the coupling reaction. In another embodiment, the ratio of cycloalkyl to phenol is at least about 1:1, in the range of 1:1 to 1.5:1, or about 1.5:1. However, equimolar amounts of phenol and cycloalkyl can be utilized. In still another embodiment, a ratio of greater than 1.5:1 can be utilized. However, in such embodiments, the excess reagent can necessitate removal of the cycloalkyl following the next step.

A carbonate salt is also utilized in the coupling reaction. A variety of carbonate salts are known in the art and can be used according to the present invention. In one embodiment, the carbonate salt has a granularity of less than about 520 μm, less than about 250 μm, less than about 100 μm, less than about 75 μm, or less than about 50 μm. In another embodiment, the carbonate salt has a granularity of 30 to 50 μm. Carbonate salts can include potassium carbonate ($K_2CO_3$) or bicarbonate, sodium carbonate or bicarbonate, cesium carbonate or bicarbonate, and lithium carbonate or bicarbonate, as well as anhydrous forms of the same. In one embodiment, the carbonate salt is potassium carbonate, potassium carbonate sesquihydrate, or potassium bicarbonate, and in another embodiment the anhydrous forms of the same.

The coupling process can also be carried out in the presence of a phase transfer agent, as described above.

In one embodiment, the solvent utilized to couple the phenol and cycloalkyl does not react with the phenol, cycloalkyl, carbonate salt, or optional phase transfer agent. In another embodiment, the solvent also does not react with the reagents utilized in subsequent steps. In one embodiment, the solvent is an ether, and in another embodiment is tetrahydrofuran. One of skill in the art would readily be able to select a suitable solvent for use in the present invention. The solvent can also contain small amounts of acetone, DMF, MeCN, water, alcohols including methanol, among others, if any. In one embodiment, the solvent contains less than about 0.05 equivalents of acetone, DMF, MeCN, water, alcohol, or combinations thereof. In another embodiment, the solvent is anhydrous.

The coupling reaction is typically performed at temperatures ranging from about room temperature to elevated temperatures. One of skill in the art would readily be able to determine the temperature required to perform the coupling reaction. In one embodiment, a temperature at or less than the boiling point of the solvent is utilized. In another embodiment, the coupling reaction is performed in THF at the boiling point of the same or at the reflux temperature of the reaction mixture.

The coupling reaction is also performed for a period of time that permits coupling of the cycloalkyl and phenol. One of skill in the art would readily be able to determine the amount of time required for the coupling to be completed using techniques known to those of skill in the art. Typically, spectroscopic techniques including chromatography, such as thin layer chromatography (TLC), gas chromatography (GC), liquid chromatography (LC), or high performance liquid chromatography (HPLC); nuclear magnetic resonance (NMR); infrared spectroscopy (IR); mass spectroscopy (MS); and combinations thereof, among others, can be utilized to determine the status of the reaction and formation of the coupled product.

In one embodiment, the cycloalkyl and phenol are combined with the other reagents in one vessel and the reaction performed in the selected solvent. Alternatively, the phenol, solvent, carbonate salt, and optional phase transfer agent are combined and the cycloalkyl added thereafter. In one embodiment, the cycloalkyl is added in one aliquot, or in two or more aliquots. In another embodiment, the cycloalkyl is added in two aliquots. The intervals between the separate additions of cycloalkyl to the phenol can be about 1 minute to about 8 hours, about 4 to about 6 hours. In one embodiment, the interval is about 6 hours. However, shorter or longer intervals can be utilized as determined by one of skill in the art Subsequent to the coupling reaction, the coupled product can be isolated as a solid or isolated in the solvent and utilized in situ in further reactions. If isolated as a solid, basic techniques known to those of skill in the art to isolate solids dissolved therein solvents can be followed and include, without limitation, extraction, precipitation, recrystallization, evaporation, drying.

The present invention includes using the coupled product in the solvent without isolating the same as a solid and is pure enough in solution to use in subsequent reactions without isolation as a solid and/or without further purification. The solvent containing the coupled product can be filtered to remove any extraneous solid materials.

The present invention provides for processes where the coupled product is produced in an about 100% yield, i.e., a quantitative yield. However, yields of about 80% to about 100% of the coupled product are expected depending upon the reaction conditions and purity of the phenol, cycloalkyl, solvent, and optional phase transfer agent.

In one embodiment, the present invention provides a process for coupling a phenol and cycloalkyl including combining an optionally substituted phenol, a cycloalkyl substituted with a leaving group, carbonate salt, and tetrahydrofuran; and isolating the coupled product.

In a further embodiment, the present invention provides a process for preparing a substituted benzaldehyde including combining a substituted phenol, a cycloalkyl substituted with a leaving group, carbonate salt, and THF; and isolating the substituted benzaldehyde.

In another embodiment, the present invention provides a process for preparing 3-cyclopentyloxy-4-methoxybenzaldehyde including combining 3-hydroxy-4-methoxybenzaldehyde, a cyclopentyl compound, a carbonate salt, and tetrahydrofuran; and isolating 3-cyclopentyloxy-4-methoxybenzaldehyde.

In a further embodiment, the present invention provides a process for preparing 3-cyclopentyloxy-4-methoxybenzaldehyde including combining 3-hydroxy-4-methoxybenzaldehyde, cyclopentyl bromide, potassium carbonate, and THF; and filtering the THF solution.

In yet another embodiment, the present invention provides a process for preparing 3-cyclopentyloxy-4-methoxybenzaldehyde including combining 3-hydroxy-4-methoxybenzaldehyde, cyclopentyl bromide, potassium carbonate, a phase transfer agent, and tetrahydrofuran; and filtering the coupled product.

In still a further embodiment, the present invention provides a product prepared according to the processes of the present invention.

III. Methods of Using the Compounds Prepared

A compound prepared according to the present invention is a key intermediate in the formation of a number of compounds, and notably, a number of biologically active compounds.

For example, a 3-cyclopentyloxy-4-methoxybenzaldehyde produced by the method of the invention is a useful intermediate for production of compounds that are selective inhibitors of PDE4. Such compounds are useful in the treatment of inflammatory diseases and other diseases involving elevated levels of cytokines, as well as central nervous system (CNS) disorders, also is disclosed. See, e.g., U.S. Pat. No. 6,716,871 [use in production of pyrrolidone compounds that are cyclic AMP-specific phosphodiesterase inhibitors]. See, U.S. Pat. No. 6,518,306 [use in production of 1,4-substituted 4,4-diaryl cyclohexanes]. Further, the 3-cyclopentyloxy-4-methoxybenzaldehyde produced by the method of the invention is a useful intermediate in production of oxime carbamates and oxime carbonates useful as bronchodilators and anti-inflammatories. See, e.g., U.S. Pat. Nos. 5,459,151 and 5,124,455.

Thus, the processes of the invention provide a method of forming a key intermediate used in the production of a number of biologically active small molecules. The processes in the 3-cyclopentyloxy-4-methoxybenzaldehyde by combining 3-hydroxy-4-methoxybenzaldehyde prepared according to the invention can be used is not a limitation of the invention.

Compounds produced using the 3-cyclopentyloxy-4-methoxybenzaldehyde by combining 3-hydroxy-4-methoxybenzaldehyde prepared according to the present invention are useful in the treatment of asthma, inflammatory disorders including psoriasis, proliferative skin disease, Crohns disease, urticaria, rhinitis, arthritis and neurogenic inflammation, and depression. Such compounds produced using the key intermediate of the invention are also useful in inhibiting phosphodiesterase (PDE) IV (PDE IV or PDE4) and treating bronchodilation, inflammation, acute or chronic bronchial asthma.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of 3-Cyclopentyloxy-5-Methoxybenzaldehyde

A 1-L flask equipped with a mechanical stirrer, nitrogen inlet, thermometer, and condenser, were charged with isovanillin (91.2 g, 0.60 mol, 1.0 equivalent) and THF (250 mL), followed by addition of Bu$_4$NBr (19.3 g, 0.06 mol, 10 mol%, 0.10 eq.) and anhydrous K$_2$CO$_3$ (124 g, 0.90 mol, 1.5 eq.). The reaction mixture was stirred vigorously and heated to reflux (about 65 to about 75° C.). Cyclopentyl bromide (89.4 g, 0.60 mol, 1.0 eq.) was added dropwise and the mixture was stirred at refluxed for 6 hours. A second portion of cyclopentyl bromide (44.7 g, 0.30 mol, 0.5 eq.) was added dropwise and stirring and heating was continued for 6 hours. The reaction solution was monitored by TLC for completion, thereby cooled to room temperature, and any remaining solids removed by filtration. The filter pad was washed with THF (2×90 mL) to remove remaining 3-cyclopentyloxy-5-methoxybenzaldehyde on the filter pad. 3-Cyclopentyloxy-5-methoxybenzaldehyde was thereby isolated in THF and its purity verified using HPLC.

Example 2

Preparation of 1-(3-Cyclopentyloxy-4-Methoxyphenyl)Ethanol

To the 3-cyclopentyloxy-4-methoxybenzaldehyde in THF solution from Example 1, 3 M methyl magnesium chloride in THF (240 mL) was added dropwise at −10 to -4° C. over 5 hours. After stirring an additional 1 hour at 0° C., HPLC showed 0.07% aldehyde remaining. The reaction mixture was slowly treated with 20% ammonium chloride (340 g) and then acidified with 10% hydrochloric acid (270 g) to a pH of 8. The layers were separated, the aqueous layer extracted with THF, and the combined extracts washed with brine. The organic solution was concentrated to give 1-(3-cyclopentyloxy-4-methoxyphenyl) ethanol as an oil (115.05 g, 81% yield, purity 94.4% by HPLC area). $^1$H-NMR: 6.93 (d, J=1.8 Hz, 1H), 6.88 (dd, J=8.2 Hz, J=1.8 Hz, 1H), 6.83 (d, J=8.2, 1H), 4.80 (m, 2H), 3.84 (s, 3H), 1.99–1.80 (m, 6H), 1.61 (m, 2H), and 1.48 (d, J=6.4 Hz, 3H). $^{13}$C-NMR: 149.2, 147.6, 138.5, 117.5, 112.3, 111.7, 80.3, 70.0, 56.0, 32.7, 25.0, and 24.0.

Example 3

Preparation of (3-Cyclopentyloxy-4-Methoxyphenyl)Methanol 1M lithium aluminum hydride in THF (1.5 mL) was added into a stirred solution of 3-cyclopentyloxy-4-methoxybenzaldehyde (1.1 g; 5 mmol) in THF solution in an ice bath. After the reaction was completed (as evidenced by TLC), the mixture was acidified with 2M HCl and extracted with ether. The organic phase was washed with water and dried over $MgSO_4$. Filtration, followed by evaporation gave (3-cyclopentyloxy-4-methoxyphenyl)methanol as an oil ( 0.9 g; 81% yield; purity 98.1% by HPLC area). $^1$H-NMR: 6.92 (s, 1H), 6.88 (d, J=8.2 Hz, 1H), 6.84 (d, J=8.1 Hz, 1H), 4.80 (m, 1H), 4.61 (s, 2H), 3.84 (s, 3H), 2.13–1.78 (m, 6H), and 1.61 (s, 2H). $^{13}$C-NMR: 149.4, 147.6, 133.6, 119.3, 114.0, 111.7, 80.3, 60.5, 56.0, 32.7, and 24.0.

Example 4

Comparison of Reagents in the Preparation of 3-Cyclopentyloxy-4-Methoxybenzaldehyde Cyclopentylbromide, a carbonate having the granularity set forth in Table 1, and any additional reagents as set forth in Table 1 were added to a stirred solution of 3-hydroxy-4-methoxybenzaldehyde (isovanillin; See column (2) below). Each reaction was monitored by TLC at 12 hours to determine the percentage conversion to the 3-cyclopentyloxy-4-methoxybenzaldehyde (I) product (See column (1) below).

These data illustrate that samples containing tetrabutylammonium bromide provide a faster conversion to product (I). These data also illustrate that the presence of potassium carbonate having a granularity of less than about 536 μm provides a faster conversion of isovanillin to the product (I) than samples containing potassium carbonate having a coarser granularity. These data also illustrate that samples further containing methanol and tetrabutylammonium bromide provide a nearly quantitative conversion to (I).

TABLE 1

| Reaction | Carbonate | Carbonate Granularity | Additional Reagents | (1) | (2) |
|---|---|---|---|---|---|
| 1 | $K_2CO_3$ | <536 μm* | $Bu_4NBr$ | 97.1 | 3.0 |
| 2 | $K_2CO_3$ | <536 μm | $Bu_4NBr$ | 88.5 | 11.6 |
| 3 | $K_2CO_3$ | <536 μm | $Bu_4NBr$ 1 eq. MeOH | 99.9 | 0 |
| 4 | $K_2CO_3$ | <536 μm | $Bu_4NBr$ 0.05 eq. MeOH | 99.5 | 0 |
| 5 | $K_2CO_3$ | <29 μm | $Bu_4NBr$ | 99.9 | 0 |
| 6 | $K_2CO_3$ | <29 μm | 0.1 eq. $H_2O$ | 54.8 | 21.4 |
| 7 | $K_2CO_3$ | <29 μm | 0.1 eq. MeOH | 56.4 | 26.4 |
| 8 | $K_2CO_3$ | <29 μm | — | 66.9 | 16.7 |
| 9 | $K_2CO_3$ | 325-mesh powder** | $Bu_4NBr$ | 99.8 | 0 |
| 10 | $K_2CO_3$ | granular+ | $Bu_4NBr$ | 62.1 | 36.9 |
| 11 | $K_2CO_3$ | granular | $Bu_4NBr$ 0.05 eq. MeOH | 60.5 | 38.8 |
| 12 | $KHCO_3$ | mortar-ground++ | $Bu_4NBr$ | 98.5 | 1.3 |
| 13 | $K_2CO_3 \cdot 1.5 H_2O$ | mortar-ground | $Bu_4NBr$ | 99.3 | 0 |

*$K_2CO_3$ having 90% of the particles below 536 μm
**$K_2CO_3$ having 90% of the particles below 48 μm (Aldrich)
+$K_2CO_3$ as a coarse powder
++$K_2CO_3$ as a coarse powder that has been mortar ground All publications listed in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A process for preparing a phenoxycycloalkyl compound, comprising the steps of:
   (i) coupling 3-hydroxy-4-methoxybenzaldehyde and a cycloalkyl compound substituted with a leaving group, in the presence of a carbonate salt and an ether; and
   (ii) isolating the product of step (i).

2. The process according to claim 1, wherein said ether in step (i) is tetrahydrofuran.

3. The process according to claim 1, wherein the product is isolated in tetrahydrofuran in step (ii).

4. The process according to claim 1, wherein said phenoxycycloalkyl compound is a substituted benzaldehyde.

5. The process according to claim 1, wherein said cycloalkyl compound is of the formula CpX, wherein X is selected from the group consisting of Br, Cl, I, OTosylate, OMesylate, and OTriflate and Cp is cyclopentyl.

6. The process according to claim 1, wherein said cycloalkyl compound is cyclopentyl bromide.

7. The process according to claim 1, wherein said phenoxycycloalkyl compound is 3-cyclopentyloxy-4-methoxybenzaldehyde.

8. The process according to claim 7, wherein said 3-cyclopentyloxy-4-methoxybenzaldehyde is greater than 99% pure.

9. The process according to claim 7, wherein said 3-cyclopentyloxy-4-methoxybenzaldehyde is dissolved in said ether.

10. The process according to claim 7, further comprising forming a pharmaceutically acceptable salt of said 3-cyclopentyloxy-4-methoxybenzaldehyde.

11. The process according to claim 1, wherein said carbonate salt is a potassium carbonate.

12. The process according to claim 11, wherein said potassium carbonate is potassium carbonate sesquihydrate or potassium bicarbonate.

13. The process according to claim 1, wherein the granularity of said carbonate salt is 30 to 50 μm.

14. The process according to claim 1, wherein said ether is anhydrous.

15. The process according to claim 1, further comprising a phase transfer agent.

16. The process according to claim 15, wherein said phase transfer agent is tetrabutylammonium bromide.

17. The process according to claim 1, wherein said process step (i) is carried out in the absence of acetone, dimethylformamide, or acetonitrile.

18. The process according to claim 1, wherein process is performed at the boiling point of said ether.

19. The process according to claim 1, wherein step (ii) comprises filtration.

20. The process according to claim 1, wherein the cycloalkyl is cyclopentyl bromide, the carbonate salt is potassium carbonate, and the product is isolated by filtration.

21. The process according to claim 20, further comprising a phase transfer agent in step (i).

22. A process for preparing 3-cyclopentyloxy-4-methoxybenzaldehyde, comprising the steps of:
   (i) coupling 3-hydroxy-4-methoxybenzaldehyde and cyclopentyl bromide, in the presence of potassium carbonate and tetrahydrofuran; and (ii) isolating the 3-cyclopentyloxy-4-methoxybenzaldehyde.

23. A process for preparing 3-cyclopentyloxy-4-methoxybenzaldehyde, comprising the steps of:
(i) coupling 3-hydroxy-4-methoxybenzaldehyde and cyclopentyl bromide, in the presence of potassium carbonate, tetrabutylammonium bromide, and tetrahydrofuran; and
(ii) isolating the 3-cyclopentyloxy-4-methoxybenzaldehyde.

* * * * *